(12) United States Patent
Jang et al.

(10) Patent No.: US 7,550,618 B2
(45) Date of Patent: Jun. 23, 2009

(54) PREPARATION OF IRON(II) ACETATE POWDER FROM A LOW GRADE MAGNETITE

(75) Inventors: Hee Dong Jang, Daejeon (KR); Yong Jae Suh, Daejeon (KR); Dae Sup Kil, Daejeon (KR); Kee Kahb Koo, Seoul (KR); Jae Kyeong Kim, Seoul (KR); Han Sang Oh, Jeju-si (KR)

(73) Assignee: Korea Institute of Geoscience & Mineral Resources, Daejeon (KR)

( * ) Notice: Subject to any disclaimer, the term of this patent is extended or adjusted under 35 U.S.C. 154(b) by 0 days.

(21) Appl. No.: 11/961,177

(22) Filed: Dec. 20, 2007

(65) Prior Publication Data

US 2009/0105493 A1    Apr. 23, 2009

(30) Foreign Application Priority Data

Oct. 18, 2007    (KR) .................. 10-2007-0104809

(51) Int. Cl.
C07F 15/02    (2006.01)
(52) U.S. Cl. ...................................... 556/147; 556/146
(58) Field of Classification Search .............. 556/146, 556/147
See application file for complete search history.

(56) References Cited

U.S. PATENT DOCUMENTS

| 2,873,289 | A | 2/1959 | MacKellar |
| 4,633,001 | A | 12/1986 | Cells |
| 5,221,657 | A | 6/1993 | Montino et al. |
| 2006/0020026 | A1* | 1/2006 | Kwok et al. ................. 514/502 |

FOREIGN PATENT DOCUMENTS

| GB | 1361284 | 7/1974 |
| KR | 100201871 B1 | 3/1999 |
| KR | 10-2005-0121426 A | 12/2005 |
| KR | 10-2006-002476 A | 1/2006 |
| RU | 2259994 C1 | 7/2005 |
| RU | 2269508 C2 | 9/2005 |
| RU | 2269509 C2 | 9/2005 |

OTHER PUBLICATIONS

Gallagher et al., American Ceramic Society Bulletin, vol. 52, No. 11, pp. 842-849 (1973).*
Redl et al., Journal of American Chemical Society, vol. 126, No. 44, pp. 14583-14599 (2004).*

(Continued)

Primary Examiner—P. Nazario Gonzalez
(74) Attorney, Agent, or Firm—The Webb Law Firm (57) ABSTRACT

The present invention relates to a preparation of iron(II) acetate powder from low grade magnetite and comprises the following steps: (a) adding organic acid to low grade magnetite powder to obtain iron solution; (b) adding hydroxide to the iron solution to obtain iron hydroxide; and (c) adding acetic acid to the iron hydroxide, thereby obtaining iron(II) acetate. According to the present invention, it is possible to obtain high purity iron(II) acetate using low grade magnetite and there are advantages of mass producible environmentally-friendly simple process and prevention of corrosion of facilities.

10 Claims, 4 Drawing Sheets

OTHER PUBLICATIONS

Lim, Journal of the Korean Magnetics Society, pp. 256-267, vol. 10, No. 5, Oct. 2000.

Chao et al., Synthesis and characterisation of nanocrystalline iron oxides via ultrasonic spray assisted chemical vapour deposition, Journal of Physics: Conferernce Series 26, (2006) pp. 304-307.

Klokkenburg et al., Direct Imaging of Zero-Field Dipolar Structures in Colloidal Dispersions of Synthetic Magnetite, J. Am. Chem. Soc. 2004,pp. 16706-16707.

Sun et al., Size-Controlled Synthesis of Magnetite Nanoparticles, J. Am. Chem. Soc. 2002, pp. 8204-8205.

Lee et al., Large-Scale Synthesis of Uniform and Crystalline Magnetite Nanoparticles Using Reverse Micelles as Nanoreactors under Reflux Conditions, Adv. Funct.Mater. 2005, vol. 15, No. 3, Mar. 2005, pp. 503-509.

Kumar et al., Fabrication of magnetite nanorods by ultrasound irradiation, Journal of Applied Physics, vol. 89, No. 11, Jun. 1, 2001, pp. 6324-6328.

Redl et al., Magnetic, Electronic, and Structural Characterization of Nonstoichiometric Iron Oxides at the Nanoscale, J. Am. Chem. Soc., vol. 126, No. 44, 2004, pp. 14583-14599.

Music et al. Mossbauer Spectroscopic and X-Ray Diffraction Study of the Thermal Decomposition of $Fe(CH_3COO)_2$ and $FeOH(CH_3COO)_2$, Journal of Radioanalytical and Nuclear Chemistry, Articles, vol. 1312, No. 1 (1988) pp. 61-71.

Filho et al., Formation of Magnetite From Non-Crystalline Iron (III) Nydroxoacetate, Reactivity of Solids, 3 (1987) pp. 241-250.

Jewur et al., Studies on the Thermal Decomposition of Ferric Acetate, Department of Chemistry, Indian Institute of Technology, Madras Jul. 21, 1976, pp. 195-200.

Pinkas et al., Sonochemical synthesis of amorphous nanoscopic iron (III) oxide from $Fe(acac)_3$, Ultrasonics Sonochemistry 15 (2008) pp. 257-264.

Kubik et al., A modified mordant technique for staining plant chromosomes, Genome vol. 46, 2003, pp. 527-528 (1935).

Adams et al., A New Method for the Preparation of Anhydrous Acetates, Kansas Academy of Science, pp. 129-130.

Min et al., Mineral Composition and Physical Characteristics of Some Low Grade Iron Ores, J. of Advanced Mineral Aggregate Composites, vol. 7, Sep. 2002, pp. 3-8.

Seo et al., The Skarnification and Fe-Mo Mineralization at Lower Part of Western Shinyemi Ore Body In Taebak Area, J. Miner. Soc. Korea 20(1), 35-46 (Mar., 2007).

Taxiarchou et al., Dissolution of hematite in acidic oxalate solutions, Hydrometallurgy vol. 44, (1997) pp. 287-299.

Lee et al., Study on the kinetics of iron oxide leaching by oxalic acid, Int. J. Miner. Process. vol. 80, 2006, pp. 144-152.

Lee et al., Iron-removal of Clay Mineral with Oxalic Acid, Shigen-to-Sozai, vol. 113, 1997, pp. 847-851.

Lee, et al., Dissolution of Iron Oxide Rust Materials Using Oxalic Acid, Shigen-to-Sozai, vol. 115, 1999, pp. 815-819.

Palmer et al. Potentiometric Determination of the Molal Formation Constants of Ferrous Acetate Complexes in Aqueous Solutions to High Temperature, J. Phys. Chem. vol. 92, No. 23, 1988, pp. 6795-6800.

Perrin, Spectrophotometric Determination of Iron as Ferric Acetate Complex, Analytical Chemistry, vol. 31, No. 7, Jul. 1959, pp. 1181-1182.

Yang et al., Solvothermal synthesis of anhydrous $\gamma$-$Mn(CH_3COO)_2$: A weak ferromagnet with an ordering temperature of 40 K and spin-glass behavior, Inorganic Chemistry Communications, vol. 8, 2005, pp. 846-849.

Cheng et al., Electronic and Molecular Structure of Anhydrous Ferrous Acetate. A weak Antiferromagnet Containing Six-Coordinate Iron (II) in Nonequivalent Environments, Inorganic Chemistry, vol. 16, No. 8, 1977, pp. 2097-2103

Zhu et al., Preparation of superhydrophilic a-$Fe_2O_3$ nanofibers with tunable magnetic properties, Thin solid Films vol. 510, 2006. pp. 271-274.

Gallagher et al., Preparation and Characterization of Iron Oxides, Ceramic Bulletin, vol. 52, No. 11, 1973, pp. 842-849.

* cited by examiner

PREPARATION OF IRON(II) ACETATE POWDER FROM A LOW GRADE MAGNETITE

TECHNICAL FIELD

The present invention relates to preparation of iron(II) acetate powder from low grade magnetites, and more particularly, to a process for the preparation of iron(II) acetate powder in which low grade magnetite powder containing mainly magnetite ($Fe_3O_4$) but also forsterite and diopside is dissolved in aqueous oxalic acid solution and metal components other than iron are separated in the form of non-soluble oxalate and hydroxide is added to the iron solution to obtain iron hydroxide and then acetic acid is added to the iron hydroxide to obtain aqueous suspension containing iron(II) acetate particles and thereafter iron(II) acetate is finally obtained by filtration and dry of the aqueous suspension.

BACKGROUND ART

Iron(II) acetate is an organic metal compound which has been used for relatively long time and is a mordant used for black, dark gray or brown dyeing. At the present day, the iron(II) acetate is very importantly used in the fields of electronic industry and metal material industry as materials for magnetite and catalyst for fabricating carbon nanotube (CNT). High purity magnetite is prepared by thermolysis of the iron(II) acetate and used in various industrial fields such as magnetic fluid, magnetic resonance imaging (MRI), magnetic storage media, medical diagnosis, magnetically guided drug delivery, magnetic-field assisted cancer therapy, printing ink, oxidation of cyclohexane and catalyst for synthesizing ammonia (L. T. Chao et al., Journal of Physics: Conference Series, 26, 304-307 (2006); M. Klokkenburg et al., J. Am. Chem. Soc., 126, 16706-16707 (2004); S. Sun et al., J. Am. Chem. Soc., 124, 8204-8205 (2002); Y. Lee et al., Adv. Funct. Mater., 15(3), 503-509 (2005); R. Vijaya et al., Journal of Applied Physics, 89(11), 6324-6328 (2001); F. Z. Redl et al., J. Am. Chem. Soc., 126, 14583-14599 (2004); S. Music et al., Journal of Radioanalytical and Nuclear Chemistry, 121(1), 61-71 (1988); P. P. A. Filho et al., Reactivity of Solids, 3(3), 241-250 (1987); S. S. Jewur et al., Thermochimica Acta, 19(2), 195-200 (1977)); LIM sang-ho, Journal of the Korean Magnetics Society, 10(5), 256-267 (2000); S. S. Jewur et al., Thermochimica Acta, 19(2), 195-200 (1977); LEE Kyu-wan et al., Korean Patent No. 10-201871; J. Pinkas et al., Ultrasonics Sonochemistry (2007), doi:10.1016/j.ultsonch.2007.03.009; F. Montino et al., U.S. Pat. No. 5,221,657 (1993)).

The magnetite has half-metal properties due to high Curie temperature (860 K) and full spin-polarization. The half-metal, in which electrons of one spin orientation exhibit metal conductivity but electrons of the opposite orientation do not exhibit the metal conductivity, exhibits a giant magneto-resistance (GMR) in that an electrical resistance of a material is significantly changed when a magnetic field is applied, and plays a very important role as a spin electronic device. Since the magnetite exhibits tunneling magneto-resistance effect (a phenomenon in that a magneto-resistance is changed as a tunnel current between an insulator and a magnetic substance is changed by a magnetic field) which shows a magneto-resistance change rate of nearly 50% in the GMR, particularly at a room temperature, the magnetite enables high density recording and reading and is applied in a magnetic head for an ultra high density hard disk drive, a Magnetic Random access memory (MRAM) and a magnetic sensor.

The carbon nanotube was first discovered in 1991 and is used in various fields such as a field-effect transistor (FET), field emission arrays, storage of hydrogen and a fuel cell due to its unique physical-chemical properties of high strength, high elastic modulus, low frictional coefficient, chemical stability and electrical conductivity. As methods for preparing the carbon nanotube, chemical vapor deposition, catalytic pyrolysis, arc discharge and laser ablation are known. The iron(II) acetate is used as an organometallic catalyst which determines length, diameter, crystallinity and density of the carbon nanotube in the process for the preparation of the carbon nanotube by chemical vapor deposition(HAN In-tek, Korean Patent Laid open 10-2005-121426; HAN In-tek et al., Korean Patent Laid open 10-2006-2476).

In the process for the preparation of the iron(II) acetate suggested long time ago by Casey, Doyle and Montino, iron powder is dissolved in acetic acid in a nitrogen atmosphere and then stirred, thereby obtaining white (or light green) iron(II) acetate. When the iron(II) acetate solution is heated with oxygen addition, the iron(II) acetate is gradually changed into dark purple and black mixture and finally becomes orange colored basic $Fe_3(OH)_2(CH_3COO)_7 2H_2O$ as the acetic acid is vaporized (T. J. Kubik, Genome, 46, 527-528 (2003); R. S. Casey and J. R. Doyle, Kirk-Othmer encyclopedia of chemical technology, vol. 12, 2nd ed., Interscience, New York, 1967; F. Montino et al., U.S. Pat. No. 5,221,657). Also, Adams et al. prepared the iron(II) acetate by cathode oxidation using acetic anhydride together with ammonium acetate as an electrolyte (M. R. Adams et al., Transactions of the Kansas Academy of Science, 38, 129-130 (1935)).

With the cathode oxidation method or a method of dissolving the iron in the acetic acid, it is possible to recover high purity iron(II) acetate. These methods are however have a disadvantage that they cannot be employed in industrial applications. The known methods for the preparation of the iron(II) acetate are not preferred in consideration that i) most iron is produced in air or in the form of iron oxide (magnetite ore) and thus includes necessarily oxygen component, ii) it is possible to industrially mass produce the iron(II) acetate in general magnetite ore rather than in pure iron.

In order to improve the above problems, there have been made studies for preparing the iron(II) acetate from magnetite ($Fe_3O_4$ or $Fe_3O_4.4H_2O$), hematite ($\alpha$-$Fe_2O_3$), maghemite ($\gamma$-$Fe_2O_3$), goethite, ($\alpha$-FeOOH), amorphous iron oxide hydrate ($Fe_3O_4.xH_2O$) and limonite ($FeO(OH).nH_2O$) which are produced in the form of a magnetite ore. Russian Patent No. 2,259,994 disclosed a process for the preparation of the iron(II) acetate from a mixture of acetic anhydride and aqueous acetic acid solution, iodine, hematite, magnetite, maghemite and $Fe_3O_4$. Reaction temperature is 80° C., reaction time is 2 hours and the yield is 72.8-99.9%. Also, Russian Patent Nos. 2,269,508 and 2,269,509 disclosed a process for the preparation of the iron(II) acetate from magnetite, iron (III) acetate and a mixture of acetic anhydride and aqueous acetic acid solution. Reaction temperature and reaction time are respectively 17° C.-25° C. and 1.8 hours, and the yield is 98.5%.

Accordingly, the present inventors found the possibility of the preparation of the iron(II) acetate from refined magnetite ore components from the Russian Patent documents and have been studying for preparing the iron(II) acetate from the magnetite ore including relatively low iron content in an economic process. As a result, the present inventors suggest a process for the preparation of high purity iron(II) acetate from low grade magnetites, which is simple, economic and mass producible.

DISCLOSURE OF THE INVENTION

It is an objective of the present invention to provide a process for the preparation of high purity iron(II) acetate from low grade magnetites, which is simple, economic and mass producible.

A process for the preparation of iron(II) acetate according to the present invention comprises the following steps: (a) adding organic acid to low grade magnetite powder to obtain iron solution; (b) adding hydroxide to the iron solution to obtain iron hydroxide; and (C) adding acetic acid to the iron hydroxide, thereby obtaining iron(II) acetate.

The low grade magnetite in the step (a) has an iron content of 30-70% by weight.

The low grade magnetite powder in the step (a) may be obtained by crushing low grade magnetite ore and it is preferable that the low grade magnetite powder contains less impurities. Therefore, process for the preparation of iron(II) acetate according to the present invention may further comprise, after crushing the low grade magnetite ore and before the step (a), the step of selectively separating ferromagnetic powder by screening using a sieve, gravity separation, dry magnetic separation, wet magnetic separation or a mixed separation method thereof, and the selectively separated ferromagnetic powder may be used as the low grade magnetite powder.

Preferably, the organic acid in the step (a) which is added to dissolve iron component contained in the magnetite powder in the step (a) and precipitates metal components other than the iron as non-soluble precipitate is oxalic acid. At this time, the metal components other than the iron are precipitated as non-soluble oxalate and the iron is dissolved in the oxalic acid. The non-soluble precipitate is removed using general filtration and thus iron solution in which the iron is dissolved is obtained.

In the step (a), in order to dissolve effectively the iron in a short time and minimize the content of impurities, 0.2M to 0.8M oxalic acid is added and the reaction is performed preferably at a temperature of 80-100° C. and also preferably in pH 0.5-2.5.

The hydroxide in the step (b) in which the hydroxide is added to the iron solution to obtain the iron hydroxide is preferably sodium hydroxide, ammonium hydroxide or a mixture thereof. Preferably, in order to obtain high purity iron hydroxide, the hydroxide is added in such an amount that the step (b) is performed in pH 3.5-4.5. The iron hydroxide produced in the aforementioned condition is separated from the mother liquor and then dried in an oven, thereby obtaining the iron hydroxide.

In the step (c) for preparing the iron(II) acetate from the iron hydroxide obtained in the step (b), it is preferable that 10-100 parts by weight of acetic acid based on 1 part by weight of the iron hydroxide is added and the reaction is performed at a temperature of 25-100° C. for high yield and short reaction time. At this time, the acetic acid may be acetic anhydride or aqueous acetic acid solution.

According to the present invention, it is possible to obtain high purity iron(II) acetate using low grade magnetites and there are advantages of mass producible environmentally-friendly simple process and prevention of corrosion of facilities.

BEST MODE FOR CARRYING OUT THE INVENTION

Practical and presently preferred embodiments of the present invention are illustrative as shown in the following Examples and Comparative Examples.

However, it will be appreciated that those skilled in the art, on consideration of this disclosure, may make modifications and improvements within the spirit and scope of the present invention.

Figure 1:
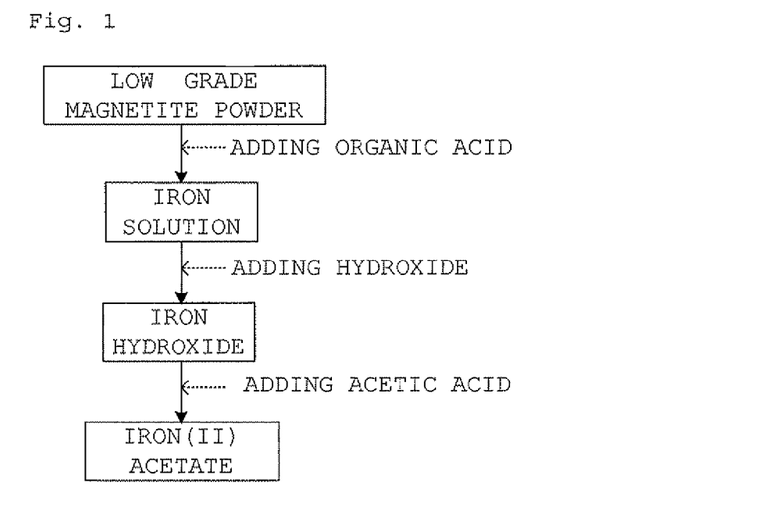
FIG. 1 is a schematic diagram illustrating a preparation process of the present invention.

In a process for the preparation of iron(II) acetate, as shown in FIG. 1, an organic acid which dissolves iron and precipitates metal other than the iron as non-soluble precipitate is added in magnetite powder obtained by crushing low grade magnetite ore and then the non-soluble precipitate is removed to obtain iron solution. Hydroxide is added to the iron solution to produce iron hydroxide precipitate. The iron hydroxide precipitate is separated from the mother liquor and then dried to obtain iron hydroxide. Thereafter, acetic acid is added to the iron hydroxide, thereby preparing iron(II) acetate.

The present invention is characterized in that it is possible to prepare the iron(II) acetate using low grade magnetite ore including 30 to 70% by weight of iron i.e. using low grade magnetite ore containing various inorganic compounds such as forsterite ($2(MgFe)SiO_2$) and diopside ($CaMg(SiO_3)_2$) as the magnetite ore instead of high purity iron compound.

It is preferable that, after crushing the low grade magnetite ore and before the step of adding the organic acid, the step of physical pretreatment usually used to obtain magnetite powder with high iron content by screening using a sieve, gravity separation, dry magnetic separation, wet magnetic separation or a mixed separation method thereof and remove nonmagnetic substances and refuses with low iron content is performed. At this time, it is preferable to use the ferromagnetic powder selectively separated in the physical pretreatment step as the magnetite powder.

By the selective separation in the physical pretreatment step, not only the magnetite powder used for the preparation of the iron(II) acetate but also additional refuses containing small amount of iron component are obtained from the low grade magnetite ore. These refuses may be separately used as cement, silicate fertilizer, aggregate for bricks, aggregate for concrete, aggregate for ceramic industry, iron oxide dye, heavy liquid material and additive for animal feed (MIN Kyoung-won et al., Journal of Advanced Mineral Aggregate Composites, 7(3), 3-8 (2002); SEQ Ji-eun at al., Journal of Mineralogical Society of Korea, 20(1), 35-46 (2007)).

The low grade magnetite ore was extracted from Sinyemi mine, Kangwon-Do, Republic of Korea and Table 1 shows the result of elemental analysis for the magnetite ore from Sinyemi mine. From the result of elemental analysis using standard wet analysis (weight measuring method), Inductively Coupled Plasma Atomic Emission Spectrophotometry (ICP-AES), Atomic absorption spectrometry (AA), it can be appreciated that the Sinyemi magnetite ore consists of $Fe_2O_3$ (52.60% by weight), MgO (21.70% by weight), $SiO_2$ (18.60% by weight), $Al_2O_3$ (2.54% by weight) and other 4.56% by weight of impurities.

TABLE 1

Result of wet elemental analysis for magnetite ore from Sinyemi mine

| Component | Content (% by weight) | Analysis method |
|---|---|---|
| $Fe_2O_3$ | 52.6 | Wet |
| MgO | 21.7 | Wet |
| $SiO_2$ | 18.6 | Wet |
| $Al_2O_3$ | 2.54 | Wet |
| MnO | 0.95 | AA |
| $K_2O$ | 0.69 | AA |
| $Na_2O$ | 0.13 | AA |
| CaO | 0.3 | Wet |
| $TiO_2$ | 0.12 | ICP-AES |
| $P_2O_5$ | 0.04 | ICP-AES |

Ore deposits in the Sinyemi mine includes east mineralized zone of zinc, lead and molybdenum and west mineralized zone of zinc, lead, molybdenum and magnetite. The west mineralized zone is a contact metamorphic deposits containing mainly magnetite but also small amount of ilmentite, sphalerite and pyrite. Geological feature of the Sinyemi mine contains limestone, lime-silicate, dolomite, shale, sandstone, quartz porphyry and quartz trachyte. Magnetite produced from the lower part of the Sinyemi has dolomite as a country rock and mainly contains magnetite-forsterite-diopside (magnesium based contact metamorphic ores). In the composition of the Sinyemi magnetite ore, a content of $SiO_2$ is largely varied in the range of 17-25% by weight and a content of $Fe_2O_3$ is also largely varied in the range of 34-59% by weight according to mixture ratio of ore, gangue and country rock. Since magnetic minerals are distributed in vast area, refuses mixed with low grade magnetite is dumped in mass at a waste rock dump or a vicinity of the mine and is not processed effectively.

Figure 2:
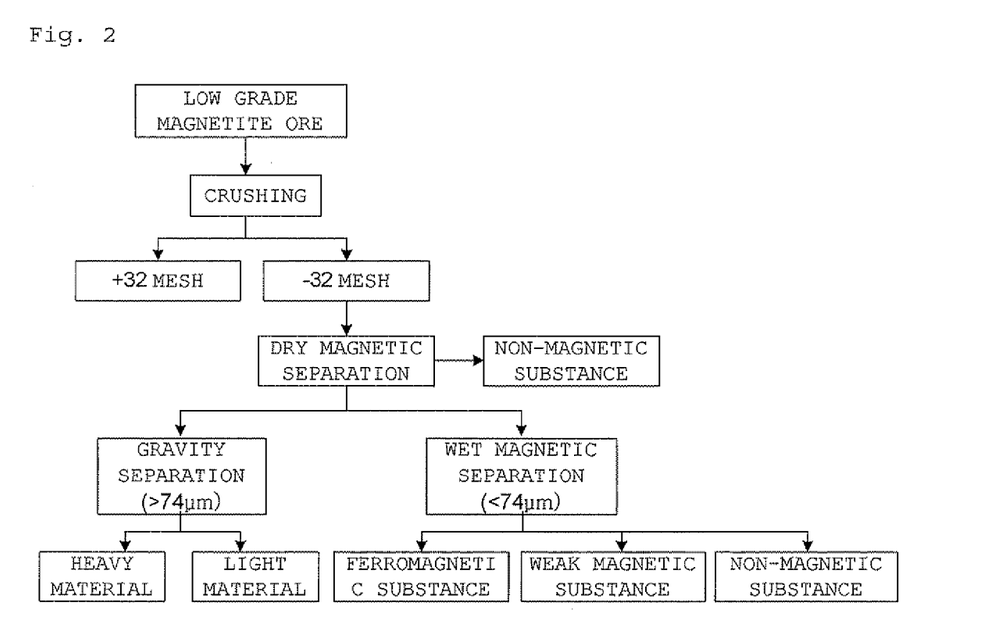
FIG. 2 is a schematic diagram illustrating a physical pretreatment step in the preparation process of the present invention.

As described in above, although it is possible to prepare iron(II) acetate using magnetite powder obtained by crushing and classifying the low grade magnetite ore, it is preferable to separate magnetic substance with high iron content by physical separations as shown in FIG. 2 and then use the separated magnetic substance as the magnetite powder.

Table 2 in below shows the result of elemental analysis for the magnetite powder obtained by gravity separation, dry magnetic separation and wet magnetic separation after crushed and classified by a jaw crusher and a pulverizer (Welte Mahltechnik, Gemany). The classified minerals were separated into magnetic minerals and non-magnetic minerals by the dry magnetic separation and the magnetic minerals were separated into heavy minerals, light minerals, ferromagnetic minerals, weak magnetic minerals and non-magnetic materials by the gravity separation and the wet magnetic separation.

TABLE 2

Result of wet elemental analysis for ore separated by dry magnetic separation, gravity separation and wet magnetic separation of magnetite ore from Sinyemi mine

| Sample | Ore % by weight | Dry magnetic separation [<0.5 mm] Non-magnetic | Gravity separation [74-500 µm] Heavy minerals | Gravity separation [74-500 µm] Light minerals | Wet magnetic separation [<74 µm] Ferro-magnetic | Wet magnetic separation [<74 µm] Weak magnetic | Wet magnetic separation [<74 µm] Non-magnetic |
|---|---|---|---|---|---|---|---|
| | | | | Content [g] | | | |
| $Fe_2O_3$ | 60.7 | 1.56 | 22.88 | 9.516 | 14.25 | 14.23 | 0.44 |
| MgO | 17.4 | 5.12 | 4.35 | 1.21 | 1.26 | 4.03 | 0.6 |
| $SiO_2$ | 15.5 | 4.98 | 3.15 | 0.79 | 0.90 | 4.03 | 0.72 |
| MnO | 1.23 | 0.18 | 0.42 | 0.16 | 0.22 | 0.32 | 0.03 |
| $Al_2O_3$ | 2.25 | 0.35 | 0.75 | 0.29 | 0.38 | 0.55 | 0.037 |
| CaO | 1.60 | 0.37 | 0.154 | 0.02 | 0.03 | 0.46 | 0.13 |
| Ratio in Ore | 100 | 13 | 32 | 12 | 17 | 24 | 2 |

As can be seen from Table 2, it is preferable to prepare the iron(II) acetate using the ferromagnetic minerals or heavy minerals with relatively high iron content and it is more preferable to prepare the iron(II) acetate using the ferromagnetic minerals separated through wet magnetic separation.

As described in above, in the magnetite powder separated through the physical pretreatment, iron component is separated from other metal impurities such as Mg, Si, Al, Mn, Ca and other rare earth metals consisting the magnetite ore through the process of dissolution and precipitation in organic acid or inorganic acid. The inorganic acid such as HCl, $HClO_4$ and EDTA used to separate and dissolve the iron component from the magnetite ore can shorten dissolution time of the magnetite ore but exhibits problems of corrosiveness to facilities and mixing of impurities due to simultaneous precipitation of various metals. On the contrary, in the case of the organic acid, i) an iron ion and an anion of the organic acid form a complex compound in the wide range of pH and thus precipitation of the iron ion is prevented, ii) oxalic acid and citric acid have a dissolution speed of magnetite ore which is an equal level to that of the inorganic acid, iii) it is possible to recycle the organic acid with high concentration generated in the pharmaceutical industry and the fermentation industry, iv) by-product generated in decomposition and dissolution process of the magnetite ore can be used as raw materials for producing fertilizer, v) there is an advantage that influence on environment due to corrosion of facility and discharge to the atmosphere is low as compared to an inorganic acid process using goethite and jarosite and vi) there is no containment of acid component and no contamination which are often generated in recovered iron compound (M. Taxiarchou et al., Hydrometallurgy, 44, 287 (1997)).

As the organic acid capable of dissolving the magnetite ore, oxalic acid, citric acid, ascorbic acid, acetic acid, tartaric acid, imidoacetic acid and fumaric acid are known from various literature sources. In the present invention, the oxalic acid which is known to have a dissolution speed relatively equal to that of the inorganic acid is used as the organic acid for recovering the iron from the magnetite ore. In the present invention, the oxalic acid may be used as an aqueous solution or an anhydrous solution. The oxalic acid is very useful in the iron recovery process since it has a high ionic strength and a strong reducing power and may be easily recycled as by-product in a chemical process, and content of residual metal component is low in the recovered iron compound (Lee et al., Int. J. Miner. Process, 80, 144-152 (2006)).

Table 3 in below shows an experimental example for a dissolution rate of magnetite powder in aqueous oxalic acid solution according to variations in pH, temperature and concentration of the aqueous oxalic acid solution.

TABLE 3

Effect of reaction temperature, concentration and pH on a dissolution rate of magnetite powder in oxalic acid and a content of impurities in precipitate

|  | Fe (%) | Mg (%) | Si (%) | Al (%) |
|---|---|---|---|---|
| Concentration (100° C., pH 1) | | | | |
| 0.25 M | 30.4 | 2.5 | 0.7 | 1.0 |
| 0.5 M | 40.4 | 0.1 | 0.8 | 1.6 |
| 1 M | 17.0 | 0.4 | 0.6 | 1.8 |
| Temperature (0.25 M, pH 1) | | | | |
| 70° C. | 7.4 | 0.1 | 0 | 1.6 |
| 80° C. | 14.7 | 0.1 | 0.0 | 1.2 |
| 90° C. | 32.7 | 1.3 | 0.3 | 1.9 |
| 100° C. | 30.4 | 2.5 | 0.7 | 1.8 |
| pH (0.25 M, 100° C.) | | | | |
| 1 | 30.5 | 3.3 | 0.8 | 1.6 |
| 2 | 22.2 | 1.9 | 0.5 | 1.2 |
| 3 | 2.1 | 1.7 | 0.0 | 1.1 |

As can be appreciated from Table 3, in order to dissolve effectively the iron in a short time and minimize the content of impurities, 0.2M to 0.8M oxalic acid is added and the reaction is performed preferably at a temperature of 80-100° C. and also preferably in pH 0.5-2.5. It is more preferable that 0.4M to 0.6M oxalic acid is added, dissolution temperature is 90-100° C. and the solution pH is 0.5-1.5. The dissolution of the iron was almost completed within 1 hour and the dissolution rate was not significantly varied even when the dissolution time is extended to 9 hours. When the concentration of the aqueous oxalic acid is more than the aforementioned preferred range, it is difficult to recover iron ion from the magnetite since hydrogen ion concentration in dissociated oxalic acid is increased and thus formation of complex salt between iron ion and oxalic acid group is promoted to produce non-soluble oxalate (LEE Seong-o et al., Journal of Min. Metall. Inst. Japan, 113, 847-851 (1997); LEE Seong-o et al., Journal of Min. Metall. Inst. Japan, 115, 815-819 (1999)); when the concentration of the aqueous oxalic acid is less than the aforementioned preferred range, the concentration of the oxalic acid is too low and thus the iron is hardly dissolved. Also, the dissolution temperature is preferably 80-100° C. since, in the temperature range, hydrogen ion concentration is increased, and absorption reaction and surface charge transfer on a surface of the magnetite become active (LEE Seong-o et al., Journal of Korean Society of Geosystem Engineering, 35, 520-526 (1998)), thereby increasing the dissolution rate of iron. When pH is more than 2.5, the dissolution rate of the iron is sharply decreased since the oxalic acid is dissociated and thus hydrogen ion which serves to precipitate the magnetite is insufficient; when pH is less than 0.5, it is difficult to recover iron ion from the magnetite since the hydrogen ion concentration is too high and thus the formation of complex salt between iron ion and oxalic acid group is promoted to produce non-soluble oxalate. Therefore it is preferable that the dissolution of the iron is performed in pH of 0.5-2.5.

Figure 3:
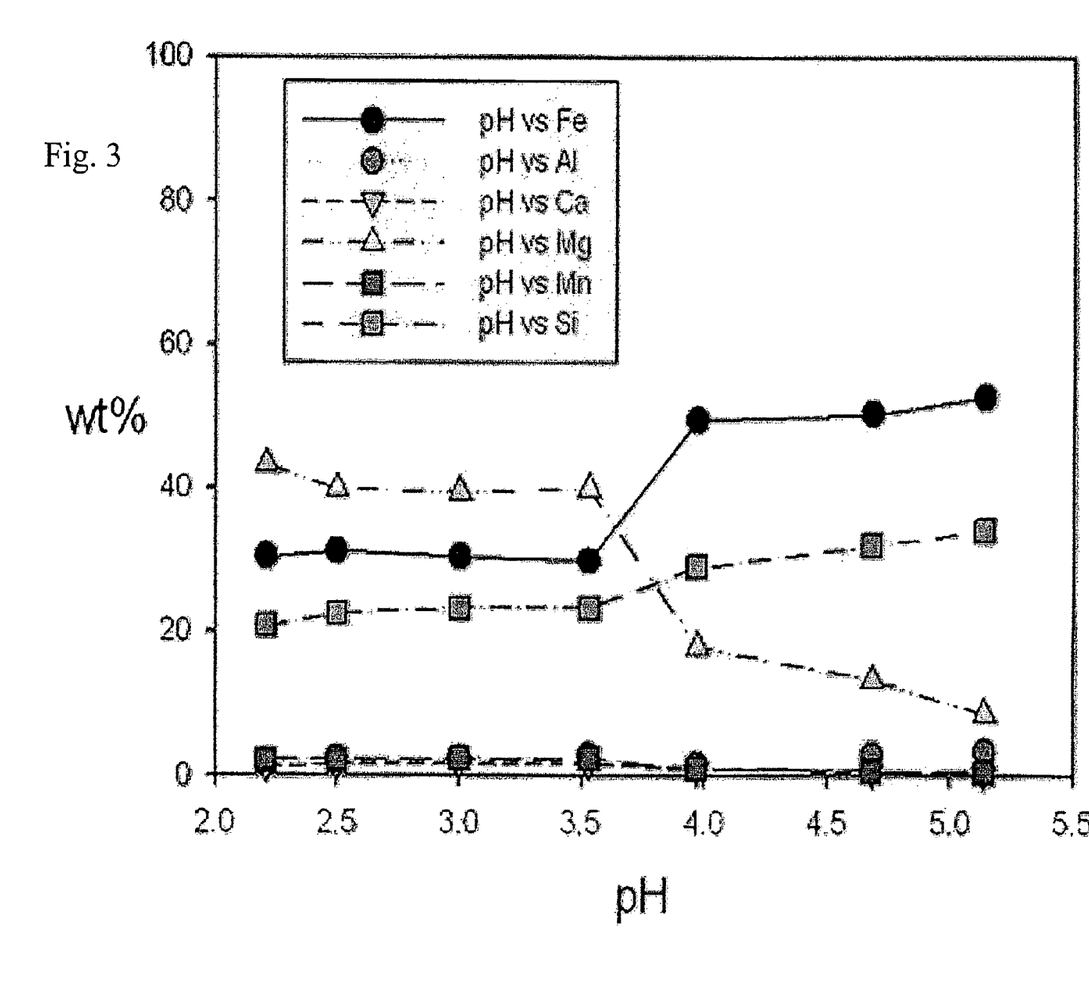
FIG. 3 is a graph illustrating result of elemental analysis for a precipitate according to variation in solution pH controlled by an amount of sodium hydroxide added in iron solution in the preparation process of the present invention.

After the iron solution is obtained using the oxalic acid with aforementioned condition, hydroxide, preferably sodium hydroxide or ammonium hydroxide is added in order to prepare iron hydroxide from the iron solution. FIG. 3 shows the result of elemental analysis for a precipitate according to variation in solution pH controlled by an amount of sodium hydroxide added in the iron solution. As can be appreciated from FIG. 3, contents of Fe and Si were increased and content of Mg was decreased as pH approaches 4. From the experimental result, it can be appreciated that it is preferable to add the hydroxide for obtaining high purity iron hydroxide so that pH of the iron solution is 3.5-4.5.

After the iron hydroxide is obtained by adding the hydroxide to the iron solution with aforementioned condition, the iron hydroxide and acetic acid are reacted and thus iron(II) acetate is finally prepared. The added acetic acid may be in the form of aqueous acetic acid solution or acetic anhydride. For high yield and short reaction time, it is preferable that 10-100 parts by weight of acetic acid based on 1 part by weight of the iron hydroxide is added and the reaction is performed at a temperature of 25-100° C. More preferably, 50-100 parts by weight of acetic acid based on 1 part by weight of the iron hydroxide is added and the reaction is performed at a temperature of 90-100° C. As 10-100 parts by weight of acetic acid based on 1 part by weight of the iron hydroxide is added, reaction time of the iron hydroxide is optimized and thus the reaction time is shortened to less than 2 hours. Also, the reaction time can be controlled by control the reaction temperature to 25-100° C. When the reaction is performed at a temperature of 25° C., it is economic since no separate heating is needed; when the reaction temperature is increased, the reaction speed is increased. At a temperature of more than 100° C. which is a boiling point of water, there is a disadvantage that water is vaporized as the reaction proceeds and thus the condition for the preparation of the iron acetate is rapidly changed. The iron(II) acetate produced by the reaction of the iron hydroxide and the acetic acid is separated from the mother liquor and then dried in a vacuum oven, thereby obtaining iron(II) acetate powder.

EXAMPLE 1

Preparation of Iron Solution 2 g of ferromagnetic powder separated from magnetite ore extracted from Sinyemi mine through the physical pretreatment of FIG. 2 and 250 ml of 0.5M aqueous oxalic solution were put into a 500 ml three-neck round bottom flask and the stirred for 1 hour (pH of the solution is 1). At this time, the temperature of the solution in the flask was controlled by heating mantle and was set to 100° C. After the stirring is completed, non-soluble components were separated and removed through a filtration to prepare iron solution.

Preparation of Iron Hydroxide 100 ml of the prepared iron solution was put into a three-neck round bottom flask and sodium hydroxide was added thereto so that pH of the iron solution is 4. When pH of the solution had reached to 4 by the addition of the sodium hydroxide, the reaction solution was filtrated to separate the resultant precipitate from the mother liquor and then the precipitate was dried in a vacuum drier to prepare iron hydroxide.

Figure 4:
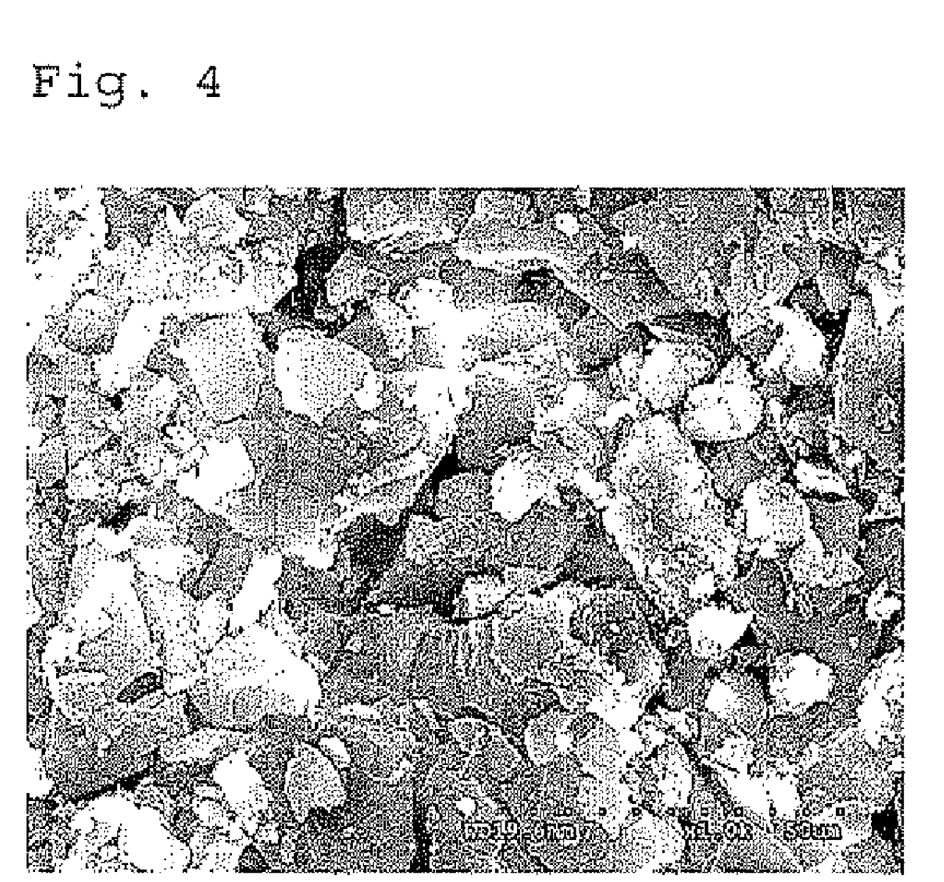
FIG. 4 is a SEM micrograph of iron(II) acetate prepared according to Example 1 of the present invention.
Figure 5:
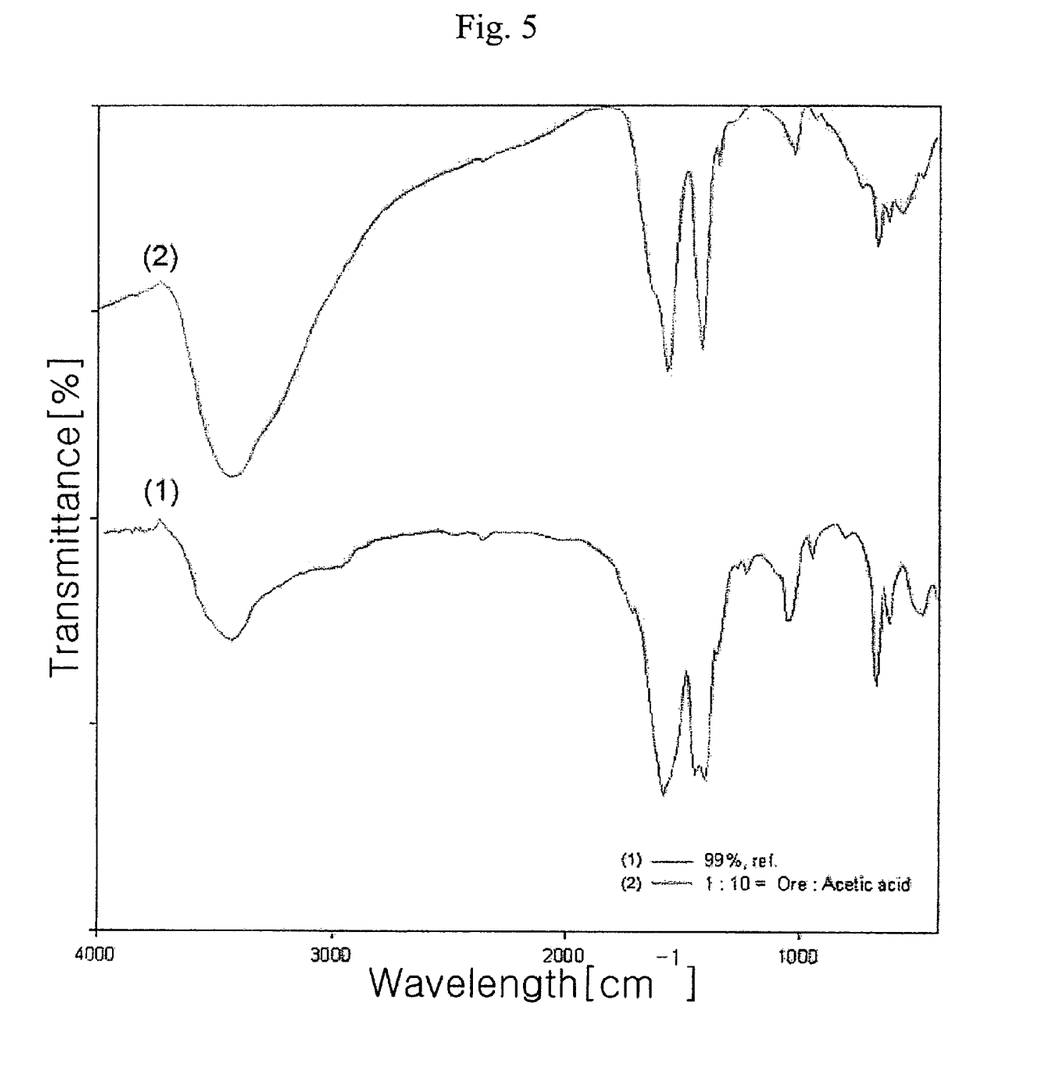
FIG. 5 is a graph illustrating result of Fourier Transform Infrared Spectra for the iron(II) acetate prepared according to Example 1 of the present invention.

Preparation of Iron(II) Acetate 1 g of the prepared iron hydroxide and 10 g of acetic acid were put into a three-neck round bottom flask and reacted at a temperature of 50° C. for 1 hour 45 minutes. Then, iron(II) acetate precipitated at the bottom of the flask was separated from the reacted mother liquor by a filtration and recovered. The recovered iron(II) acetate particles were washed with distilled water until pH of the washed liquid had reached to 7. After the completion of the washing, the iron(II) acetate particles were dried in a vacuum oven in nitrogen atmosphere to prepare iron(II) acetate. FIG. 4 is a SEM micrograph (S-4300, Hitachi, Japan) of the prepared iron(II) acetate and FIG. 5 shows the analysis result for a functional group of the dried iron(II) acetate using a Fourier Transform Infrared Spectroscope (Nicolet 380, Thermo Electron Co.). In FIG. 5, (1) is a spectra for commercially sold iron acetate with a purity of 99% and (2) is a spectra for the iron acetate prepared in the Example 1.

EXAMPLE 2

Iron(II) acetate was prepared using the same method as the Example 1 except that 1 g of iron hydroxide prepared in the Example 1 and 100 g of acetic acid were put into a three-neck round bottom flask and reacted at a temperature of 25° C. for 24 hour.

INDUSTRIAL APPLICABILITY

According to the present invention, it is possible to provide higher value-added organic metal compound (iron(II) acetate) from low grade magnetite as well as to use refuse with small amount of iron component, which is obtained as by-product, as cement, silicate fertilizer, aggregate for bricks, aggregate for concrete, aggregate for ceramic industry, iron oxide dye, heavy liquid material and additive for animal feed.

Also, iron(II) acetate prepared by the method of the present invention can be used in the fields of electronic industry and metal material industry as materials for magnetite and catalyst for fabricating carbon nanotube (CNT). High purity magnetite prepared by thermolysis of the iron(II) acetate is used in various industrial fields such as magnetic fluid, magnetic resonance imaging (MRI), magnetic storage media, medical diagnosis, magnetically guided drug delivery, magnetic-field assisted cancer therapy, printing ink, oxidation of cyclohexane and catalyst for synthesizing ammonia.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A process for the preparation of iron(II) acetate, comprising the following steps:
   (a) adding organic acid to low grade magnetite powder to obtain iron solution;
   (b) adding hydroxide to the iron solution to obtain iron hydroxide; and
   (c) adding acetic acid to the iron hydroxide, thereby obtaining iron(II) acetate.

2. The process for the preparation of iron(II) acetate as set forth in claim 1, wherein the low grade magnetite in the step (a) has an iron content of 30-70% by weight.

3. The process for the preparation of iron(II) acetate as set forth in claim 1, wherein the organic acid in the step (a) is oxalic acid.

4. The process for the preparation of iron(II) acetate as set forth in claim 3, wherein in the step (a), 0.2M to 0.8M oxalic acid is added and the reaction is performed at a temperature of 80-100° C.

5. The process for the preparation of iron(II) acetate as set forth in claim 4, wherein the step (a) is performed in pH 0.5-2.5.

6. The process for the preparation of iron(II) acetate as set forth in claim 1, wherein the hydroxide in the step (b) is sodium hydroxide, ammonium hydroxide or a mixture thereof.

7. The process for the preparation of iron(II) acetate as set forth in claim 6, wherein the step (b) is performed in pH 3.5-4.5.

8. The process for the preparation of iron(II) acetate as set forth in claim 1, wherein in the step (c), 10-100 parts by weight of acetic acid based on 1 part by weight of the iron hydroxide is added.

9. The process for the preparation of iron(II) acetate as set forth in claim 8, wherein the step (c) is performed at a temperature of 25-100° C.

10. The process for the preparation of iron(II) acetate as set forth in claim 1, further comprising, before the step (a), the step of crushing low magnetite ore and then separating ferromagnetic particles.

\* \* \* \* \*